US005208463A

United States Patent [19]
Honma et al.

[11] Patent Number: 5,208,463
[45] Date of Patent: May 4, 1993

[54] METHOD AND APPARATUS FOR DETECTING DEFORMATIONS OF LEADS OF SEMICONDUCTOR DEVICE

[75] Inventors: Makoto Honma, Tokyo; Sotozi Hiramoto, Chiba; Seiji Hata, Ayauta; Masamichi Tomita, Niihari; Akira Ishibashi, Tokyo, all of Japan

[73] Assignee: Hitachi, Ltd., Tokyo, Japan

[21] Appl. No.: 740,605

[22] Filed: Aug. 5, 1991

[30] Foreign Application Priority Data

Aug. 24, 1990 [JP] Japan ................................ 2-221302

[51] Int. Cl.⁵ .......................................... G01N 21/86
[52] U.S. Cl. ..................................... 250/561; 356/394
[58] Field of Search ............... 250/560, 561; 356/237, 356/392, 393, 394

[56] References Cited

U.S. PATENT DOCUMENTS

| | | | |
|---|---|---|---|
| 4,739,175 | 4/1988 | Tamura | 250/561 |
| 4,772,125 | 9/1988 | Yoshimura et al. | |
| 4,875,779 | 10/1989 | Luebbe et al. | 356/394 |

FOREIGN PATENT DOCUMENTS

| | | |
|---|---|---|
| 0222072 | 5/1987 | European Pat. Off. |
| 50-3674 | 11/1975 | Japan |
| 56-36004 | 4/1981 | Japan |
| 61-31909 | 2/1986 | Japan |
| 61-95203 | 5/1986 | Japan |
| 62-79644 | 4/1987 | Japan |
| 62-269047 | 11/1987 | Japan |
| 63-5243 | 1/1988 | Japan |

Primary Examiner—David C. Nelms
Attorney, Agent, or Firm—Fay, Sharpe, Beall, Fagan, Minnich & McKee

[57] ABSTRACT

Method and apparatus for detecting vertical and horizontal deformations of leads of a semiconductor device by illuminating the leads with a planar light beam and determining relative positions of the planar light beam on the leads on the basis of distribution of light rays reflected from the leads. Different lead deformations can be detected with one and the same mechanism within a short time. By applying the invention to a semiconductor device mounting apparatus, a single detector can be employed in common both for the detection of the semiconductor device position and the detection of reflections of the planar beam.

9 Claims, 9 Drawing Sheets

F I G. 12A
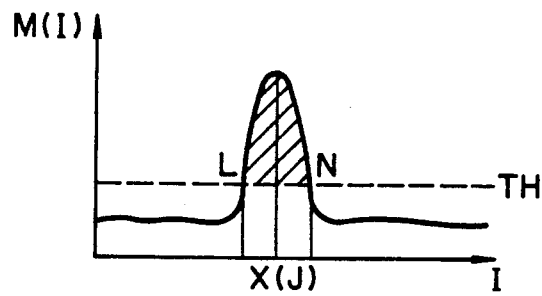
F I G. 12B
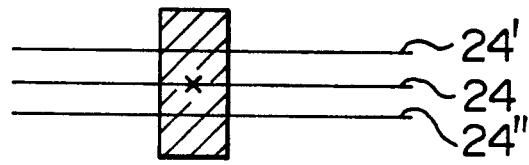
F I G. 13
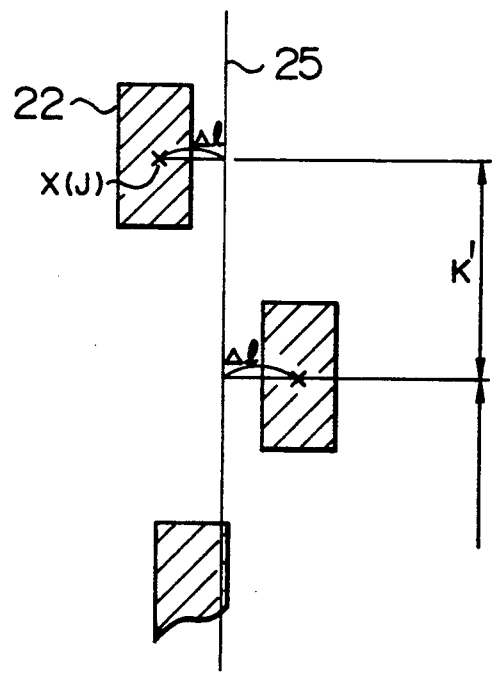

F I G. 16A
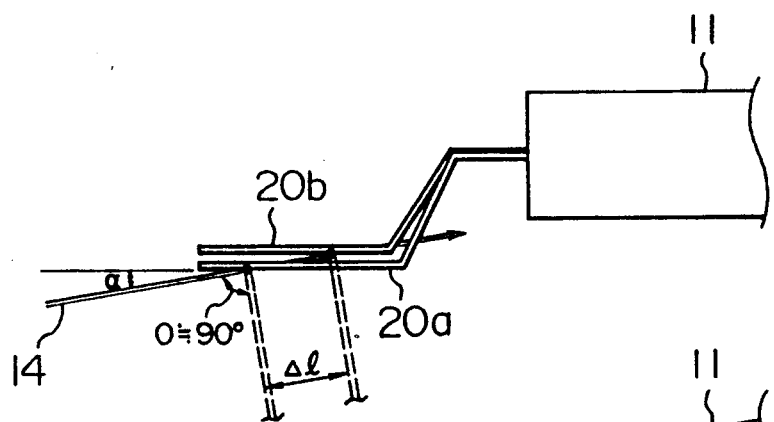
F I G. 16B
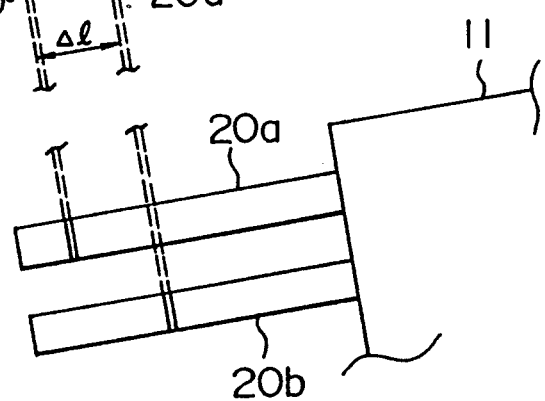

METHOD AND APPARATUS FOR DETECTING DEFORMATIONS OF LEADS OF SEMICONDUCTOR DEVICE

BACKGROUND OF THE INVENTION

The present invention relates generally to detection of deformed leads of semiconductor devices. More particularly, the invention is concerned with a method and an apparatus for detecting vertical and/or horizontal deformation (such as misorientation, abnormal bending, floating or the like, i.e. irregular states) of leads of a semiconductor device.

Heretofore, in implementation of various electronic circuits, there has widely been adopted such a device structure in which a printed wiring substrate is used for mounting thereon a semiconductor device. At present, this kind of electronic device is generally manufactured by using an automated manufacturing or mounting apparatus.

In conjunction with the automated manufacturing of the electronic devices, it is noted that the presence of deformed leads in a semiconductor device to be mounted on a printed wiring substrate provides an obstacle to realization of correct connections between the leads of the semiconductor device and the wiring patterns printed on the substrate. As typical ones of such deformation of the leads, there may be mentioned vertical deformation (i.e. deformation in the direction in which the leads extend, such as rowwise misorientation), horizontal deformation (i.e. deformation in the direction in which the semiconductor device extends, such as abnormal bending) and the like irregularities. In order to evade such obstacles, it is necessary to inspect in advance the leads of a semiconductor device for the presence of the abovementioned deformations so that only semiconductor devices having lead wires attached in the correct state are allowed to be positioned or placed on the printed wiring substrate.

Before entering into a description of the inspection or detection of such deformations or irregularities of the leads of a semiconductor device, elucidation will be made in detail of the vertical and the horizontal deformations of the leads by reference to FIGS. 1 and 2 of the accompanying drawings, in which FIG. 1 is a top plan view of a typical flat package IC device and FIG. 2 is a side elevational view of the same. In these figures, a reference numeral 2 denotes generally lead wires or leads for short, wherein leads suffering from the vertical deformation are designated by reference symbols 2a and 2b while those undergone the horizontal deformation are designated by reference symbols 2c and 2d, respectively. As mentioned above, the phrase "vertical deformation" is contemplated to mean misorientation of the leads in the rowwise or columnwise direction in which the individual leads are to extend in an orderly orientation, while the phrase "horizontal deformation" is used to mean deformation of the lead in the direction orthogonal to the rowwise or columnwise direction such as irregular or abnormal bending of the leads. The former deformation may also be referred to as misoriented deformation with the latter being termed bending deformation.

Now, in accompanying the trend of higher density implementation of the semiconductor device and miniaturization thereof, the lead wires of a semiconductor device tend to increase in the number with the inter-lead space (lead pitch, to say in another way) being more and more decreased. Under the circumstances, the vertical and horizontal deformations of the lead wires may frequently bring about formation of short-circuits between adjacent electrodes on the printed wiring substrate or render it impossible or at least extremely difficult to solder correctly the leads to the electrodes formed on the printed substrate upon mounting of the semiconductor device, which ultimately results in failure of contact or connection, thus giving rise to a serious problem in respect to the reliability of the connection.

As an attempt to overcome the problems mentioned above, there have already been proposed methods of detecting the vertical and horizontal deformations of the leads of semiconductor devices, typical ones of which are disclosed in JP-A-63-5243 and JP-A-62-79644 and shown in FIGS. 3 and 4 of the accompanying drawings, respectively.

In FIG. 3, a reference numeral 3 denotes a semiconductor device, 4 denotes a head for holding the semiconductor device 3, and a numeral 5 denotes an image pick-up device such as a camera used for detecting the deformations of leads 6 of the semiconductor device 3.

The principle underlying the lead deformation detection method shown in FIG. 3 resides in that one-dimensional pattern data representing an image of the lead array along a line in a plane transversal thereto is obtained from the output of the camera 5 which is positioned to pick up light rays reflected from the semiconductor device and the leads under inspection. The pitch of the density patterns (dark and bright patterns) which appears in the one-dimensional pattern data in dependence on the intensities or quantities of the picked-up light rays is determined for thereby detecting the deformations of the leads on the basis of variations in the pitch.

On the other hand, in FIG. 4, a reference numeral 7 denotes a semiconductor device, 8 denotes a light projector for illuminating the leads of a semiconductor device under inspection with a light beam, 9 denotes a one-dimensional position detector and 10 denotes the leads.

The principle of the lead deformation detecting method illustrated in FIG. 4 is seen in that reflected light pulses resulting from illumination of the leads 10 with the light beam are received by the detector 9, wherein the deformations of the leads of the semiconductor device are determined on the basis of the inter-pulse interval and the intensities or quantities of the reflected light pulses.

In the case of the deformation detecting method illustrated in FIG. 3, the horizontal deformation (2c in FIG. 2) is detected on the basis of difference in the length among the projecting leads. Consequently, intrinsic variance in the length of the leads 6 affects the result of measurement, making it difficult to detect the horizontal deformation with a high accuracy.

On the other hand, in the case of the deformation detecting method shown in FIG. 4, detection is susceptible to the influence of the surface states of the lead wires because the detection is based on the quantities of light reflected from the leads, thus giving rise to a problem in respect to the reliability and consistency of the results of detection. Besides, in order to detect the vertical and the horizontal deformations of all the leads, it is necessary to move the light beam projector 8 together with the one-dimensional position detector 9 for scanning the leads with the light beam or alternatively to move the semiconductor device 7, which means that the time involved in the inspection will intolerably be increased. Besides, inaccuracy, if any, in the scanning or positioning of the light beam projector 8 and the detector 9 affects adversely the detection of the vertical and the horizontal deformations of the leads, to another disadvantage.

SUMMARY OF THE INVENTION

It is therefore an object of the present invention to overcome the disadvantages and problems of the prior art lead deformation detecting methods described above and provide a method and an apparatus which are capable of detecting the vertical and horizontal deformations of leads of a semiconductor device with significantly improved accuracy with the time taken for the detection being remarkably shortened.

Another object of the present invention is to provide a method and an apparatus for detecting the deformations of the leads of semiconductor devices which apparatus can be realized in a much simplified and inexpensive structure by using one and the same detector in common as a semiconductor device position detector and a lead image pick-up device in a semiconductor device mounting apparatus to which the invention is applied.

To this end, in a mode for carrying out the invention, there is adopted a so-called light section method which itself has heretofore been known as a method of detecting three-dimensional configurations, as is typically disclosed in Japanese Patent Publication No. 36374/1975, JP-A-56-326004 and JP-A-61-95203.

The principle underlying the detection of three-dimensional or cubic shapes based on the light section method resides in that an object of concern having a cubic configuration is illuminated with a planar light beam which is shaped by using a slit so as to have a slit-like cross-section, wherein a light image resulting from projection of the light beam onto the object is picked up by an image pick-up device such as a television camera disposed at a position remote from that of a planar light beam projector, and distances between positions of concern on the object are determined in accordance with a triangulation method, as is disclosed, for example, in JP-A-50-36374. In the following description of the invention, the light beam will also be referred to as the lead sectioning planar light beam or simply as the planar light beam, while light images resulting from projection of the sectioning light beam onto objects (i.e. leads) to be inspected will be referred to as light-sectioned illuminated regions or simply as illuminated sections or regions. In this conjunction, it should be noted that the planar light beam need not necessarily be produced by passing a source light beam through a slit but may be produced by passing it through a cylindrical lens or by resorting to any other suitable means capable of emitting a light beam having a slit- or stripe-like cross-section.

In view of the abovementioned and other objects which will be apparent as description proceeds, it is proposed according to an aspect of the present invention that leads of a semiconductor device under inspection are illuminated with the sectioning planar light beam, whereon illuminated regions or sections of the leads are picked up by an image pick-up device. On the basis of distribution of the illuminated regions or sections of the leads as picked up, at least one of the vertical and the horizontal deformations is detected. In other words, three-dimensional information of the leads is obtained in accordance with the triangulation method from the distribution of the illuminated lead regions or sections resulting from illumination of the leads of a semiconductor device with the sectioning planar beam. On the basis of the position information, there can be detected the horizontal deformation as well as the vertical deformation of the leads of a semiconductor device.

BRIEF DESCRIPTION OF THE DRAWINGS

FIGS. 12A and 12B are views for illustrating a method of detecting a statistically weighted average position of a lead region illuminated with a sectioning light beam;

FIG. 13 is a diagram for illustrating a positional relation among the statistically weighted average positions of deformed lead sections illuminated with the sectioning light beam;

FIGS. 16A and 16B are views for illustrating a further embodiment of the lead deformation detecting apparatus according to the invention.

DESCRIPTION OF THE PREFERRED EMBODIMENTS

Now, the present invention will be described in detail in conjunction with exemplary or preferred embodiments thereof by reference to the accompanying drawings.

Figure 5:
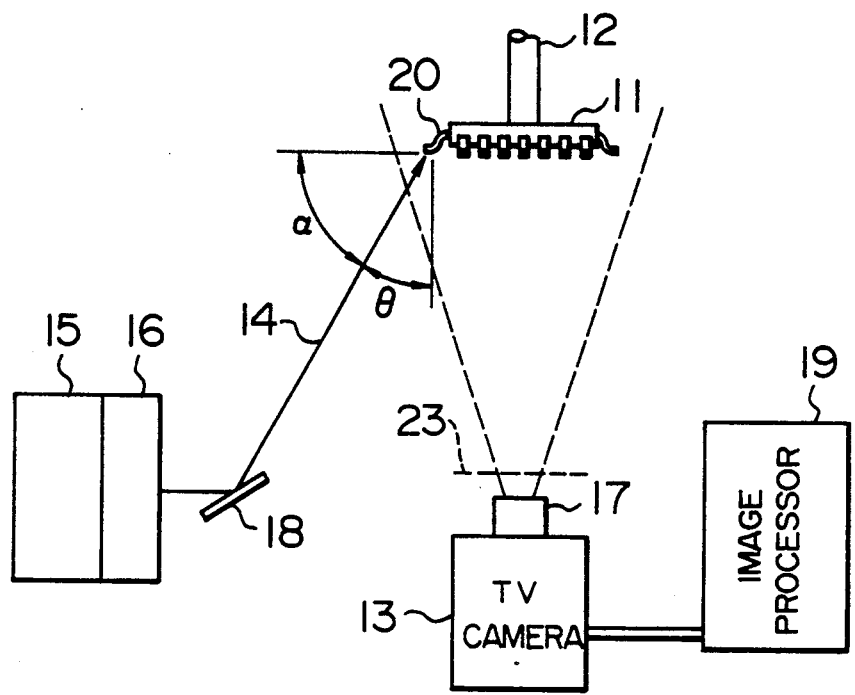
FIG. 5 is a schematic elevational view showing a general arrangement of an apparatus for detecting vertical and horizontal deformations, if any, of leads of a semiconductor device according to an embodiment of the invention.

FIG. 5 is a schematic diagram showing a general arrangement of an apparatus for detecting vertical and horizontal deformations of lead wires of a semiconductor device according to an embodiment of the invention. In general, this lead deformation detecting apparatus is so arranged that surfaces of leads 20 of a semiconductor device 11 which are to be soldered to a printed wiring substrate (not shown) are illuminated with a sectioning light beam 14 obliquely from the underside, wherein the images of the leads being illuminated with the sectioning light beam are picked up by an image pick-up device 13 such as a television camera which is disposed or oriented in a direction perpendicular to a plane corresponding to the lower surface of the semiconductor device 11.

Figure 6:
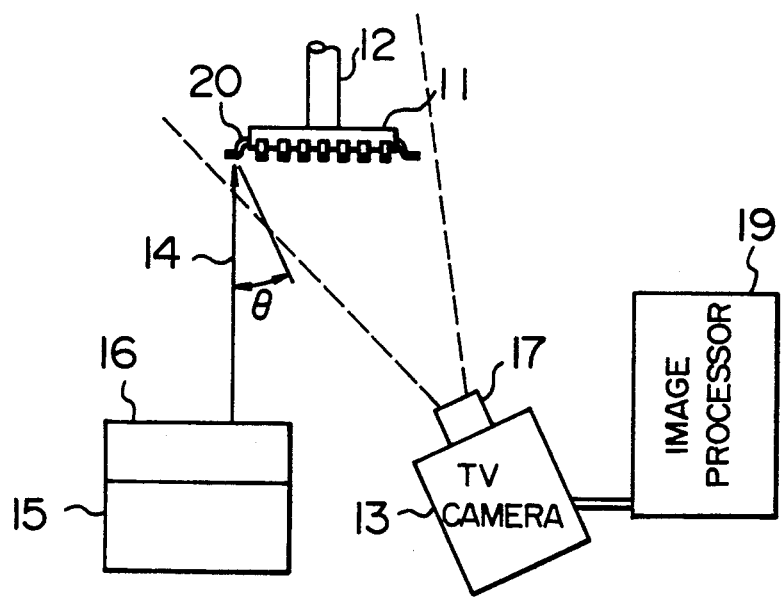
FIG. 6 is a view similar to FIG. 5 and shows a general arrangement of a lead deformation detecting apparatus according to another embodiment of the invention.

FIG. 6 is a view similar to FIG. 5 and shows the lead deformation detecting apparatus according to another embodiment of the invention. The apparatus shown in FIG. 6 is generally so arranged that the surfaces of the leads 20 of the semiconductor device 11 at which the leads are to be soldered to the printed wiring substrate (not shown) are illuminated with the sectioning light beam 14 in the direction perpendicular thereto, wherein the images of the leads being illuminated are picked up by the image pick-up device 13 disposed below the semiconductor device with an oblique angle relative to the plane coinciding with the lower surface of the semiconductor device 11.

In both of FIGS. 5 and 6, a reference numeral 12 denotes a semiconductor device holder, 13 denotes a television camera serving as the image pick-up device, 15 denotes a semiconductor laser light source serving as a light source of the sectioning beam light 14, 16 denotes a cylindrical lens for converting a linear laser light beam into a planar light beam having a slit-like cross-section, 17 denotes an optical system of the television camera, 18 denotes a mirror for reflecting the sectioning light beam, and a numeral 19 denotes an image processor unit.

In operation of the lead deformation detecting apparatus shown in FIGS. 5 and 6, a semiconductor device 11 to be inspected with regard to possible deformations of the leads 20 is first moved to a location within the field of view of the television camera 13 by means of the semiconductor device holding mechanism 12 in precedence to illumination of the leads 20. In this state, image data of the semiconductor device outputted from the television camera 13 are processed by the image processor 19 to thereby determine the center position of the semiconductor device 11 and an inclination thereof relative to a printed wiring pattern on a substrate on which the semiconductor device is to be mounted. Subsequently, the light rays produced by the semiconductor laser source 15 are shaped into the planar sectioning light beam 14 by the cylindrical lens 16, and the semiconductor device 11 under inspection is moved relative to the sectioning light beam 14 which is fixed in the illuminating position and direction by utilizing the information about the center position and the inclination determined as mentioned above so that the leads 20 of the semiconductor device 11 can be illuminated with the sectioning light beam 14. As an alternative, the sectioning light beam 14 may of course be moved so that the leads 20 of the semiconductor device 11 can correctly be illuminated. At any rate, either the semiconductor device 11 or the sectioning light beam 14 can be moved relative to the other so far as the leads 20 of the semiconductor device 11 can correctly be aligned with the illuminating position of the sectioning light beam 14. The images of the lead wires 20 thus illuminated with the sectioning light beam 14 can be picked up by the television camera 13 to be fetched and stored in the image processor 19 as the image data.

Figure 7A:
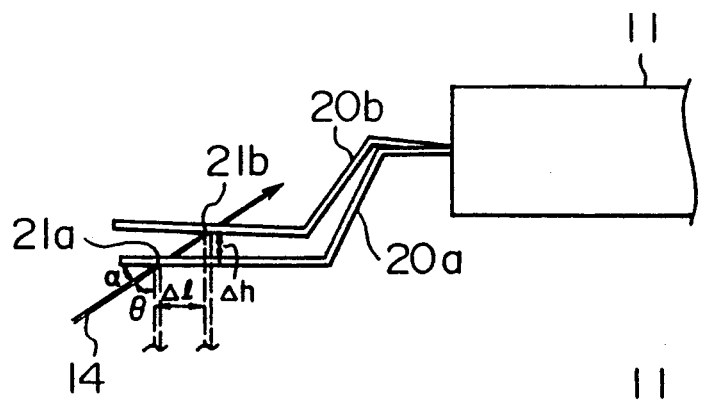
FIGS. 7A and 7B are side and plan views of a semiconductor device, respectively, for illustrating in what manner a normal lead and a horizontally deformed lead are illuminated with a sectioning light beam in the case of the apparatus shown in FIG. 5.
Figure 7B:
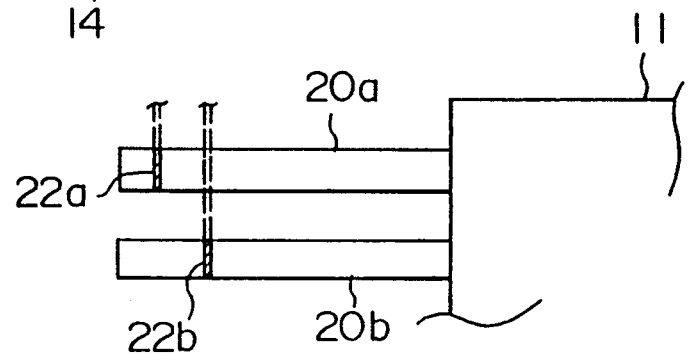

FIGS. 7A and 7B are side and plan views, respectively, of the semiconductor device 11 for illustrating in what manner image data is obtained when a lead 20 of the semiconductor device 11 which suffers from horizontal deformation (abnormal bending) is illuminated with the sectioning light beam 14 in the state where the lower surfaces of the leads 20 are illuminated with the sectioning light beam 14 obliquely from below, as described previously by reference to FIG. 5. In FIGS. 7A and 7B, a normal lead is designated by 20a with the horizontally deformed (abnormally bent) lead being designated by a reference symbol 20b.

As can be seen in FIGS. 7A and 7B, the sectioning light beam 14 intersects with the leads 20a and 20b at positions 21a and 21b, respectively. To say in another way, illuminations of the lead regions or sections 22a and 22b with the sectioning light beam can be observed or viewed with the aid of the television camera 13.

In the case illustrated in FIGS. 7A and 7B, the position of the illuminated region 22b of the horizontally deformed lead 20b is deviated from the position of the illuminated region 22a of the normal lead 20a by a deviation of $\Delta l$.

Thus, by extracting from the image data only the data of the illuminated lead sections 22a, 22b, 22c, etc. (collectively denoted by 22), the vertical and/or the horizontal deformations of the leads 20 as well as magnitude thereof can arithmetically be determined.

Figure 1:
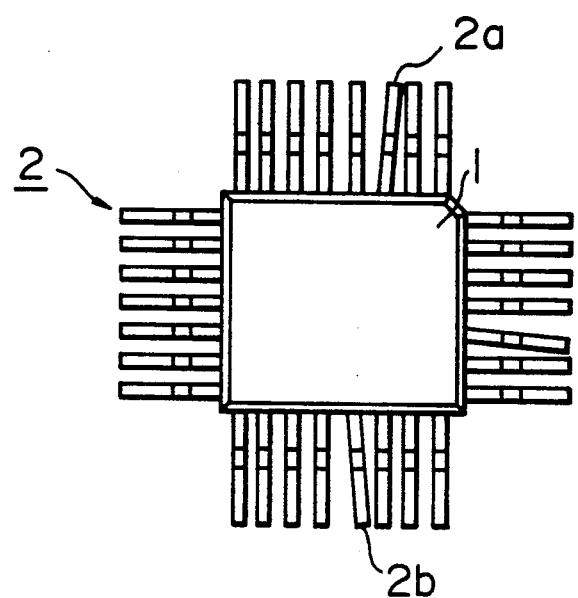
FIG. 1 is a top plan view of a flat package IC device for illustrating a vertical deformation of leads thereof.
Figure 2:
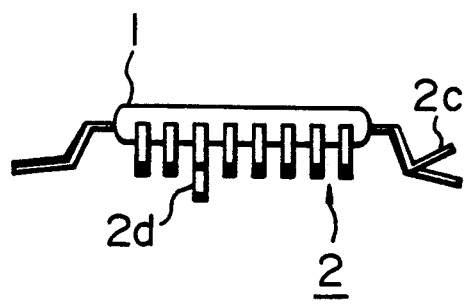
FIG. 2 is a side elevational view of the same for illustrating a horizontal deformation of the leads thereof.
Figure 3:
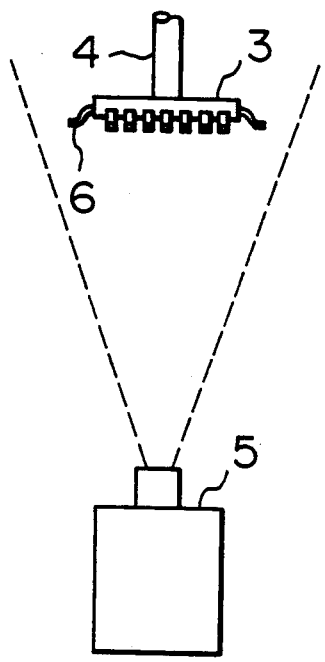
FIGS. 3 and 4 are schematic diagrams for illustrating prior art lead deformation detecting methods, respectively.
Figure 4:
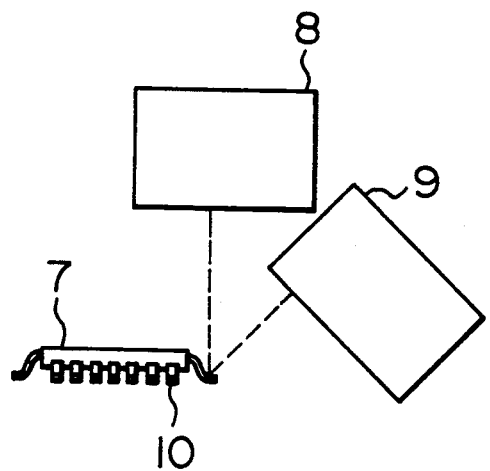

For extracting the regions or sections 22 of the leads 20 illuminated with the planar light beam 14, there may be adopted one of the methods mentioned below:

1) a method according to which the sectioning light beam is produced by using a monochromatic light source, wherein the light rays of wavelengths other than that of the light source are cut off by using a filter 23, as shown in FIG. 5, and
2) a method in which the image data obtained before illumination of the leads 20 with the planar light beam 14 is saved, wherein differences of the image data from those obtained when the leads are illuminated with the light beam 14 are determined to thereby make available only the image data concerning the regions 22 of the leads 20 which have been illuminated with the sectioning light beam 14.

Figure 8A:
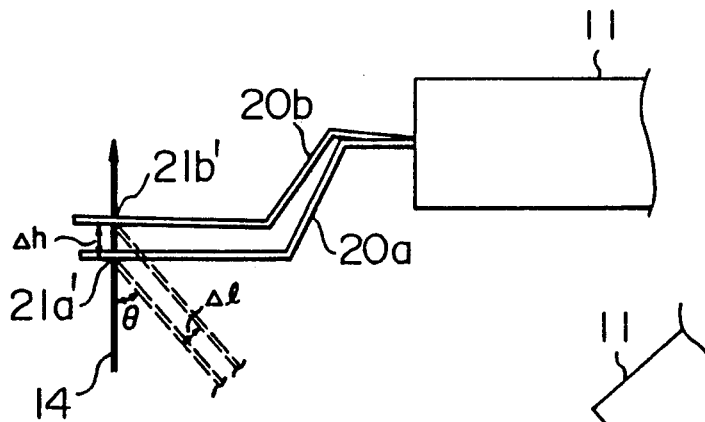
FIGS. 8A and 8B are views similar to FIG. 7A and 7B, respectively, except that the apparatus shown in FIG. 6 is employed.
Figure 8B:
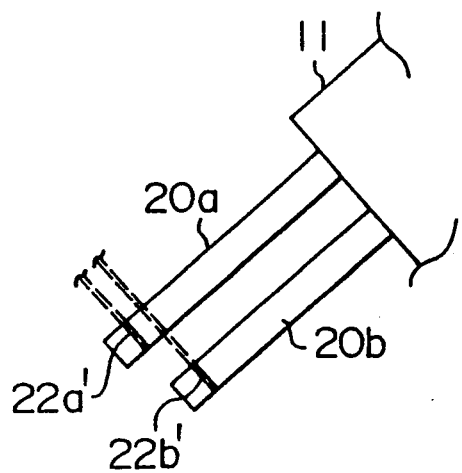

FIGS. 8A and 8B are views for illustrating in what manner the leads 20a and 20b of the semiconductor device 11 are illuminated with the sectioning light beam 14 in accordance with the method illustrated in FIG. 6 together with the states of the lead regions illuminated with the light beam 14, as picked up by the television camera. In this case, there can be obtained distributed image data of the lead sections illuminated with the light beam 14, as with the case of the method described above by reference to FIGS. 7A and 7B.

Figure 9A:
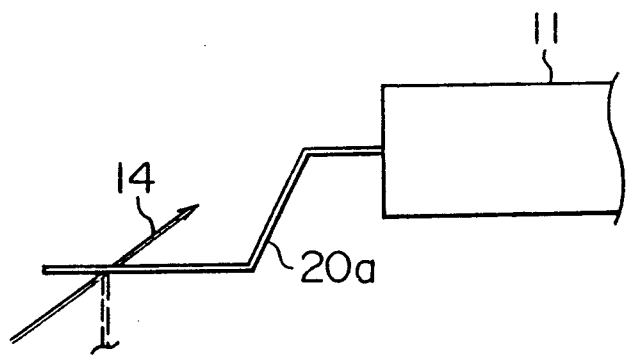
FIGS. 9A and 9B are side and plan views of a semiconductor device, respectively, for illustrating in what manner a normal lead and a vertically deformed lead are illuminated with a sectioning light beam in the case of the apparatus shown in FIG. 5.
Figure 9B:
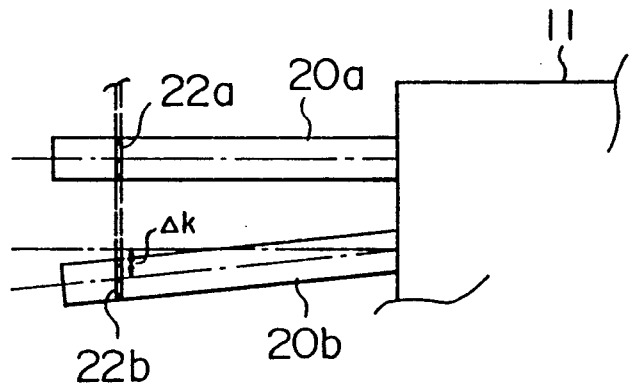

FIGS. 9A and 9B are views for illustrating in what manner a lead suffering vertical deformation or misorientation is illuminated with the sectioning light beam 14 in accordance with the method illustrated in FIG. 5 and the state of the lead regions illuminated to be picked-up by the television camera. As seen in these figures, there can be obtained distributed image data in which the image of the lead 20b suffering from the vertical deformation is deviated relative to the position of the normal lead by ΔK. It will readily be understood that similar distributed image data of the illuminated leads suffering vertical deformation can equally be obtained by using the arrangement shown in FIG. 6 as well, although illustration is omitted.

Figure 10:
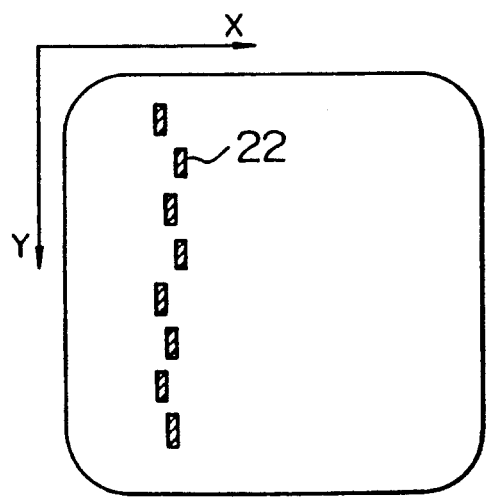
FIG. 10 is a view showing, by way of example, a distribution of image data of regions or sections of leads of a surface mounting IC device which is obtained when the leads are illuminated with a sectioning light beam.

FIG. 10 is a view showing an example of the distributed image data of the illuminated lead sections or regions 22 obtained in the manner described above. As will be seen from this figure, variance is observed in respect to the positions of the illuminated lead sections in dependence on the vertical and horizontal deformations of the lead wires. Thus, it is possible to detect or identify the vertical and horizontal deformations by evaluating the distribution of the illuminated lead section data.

Figure 11:
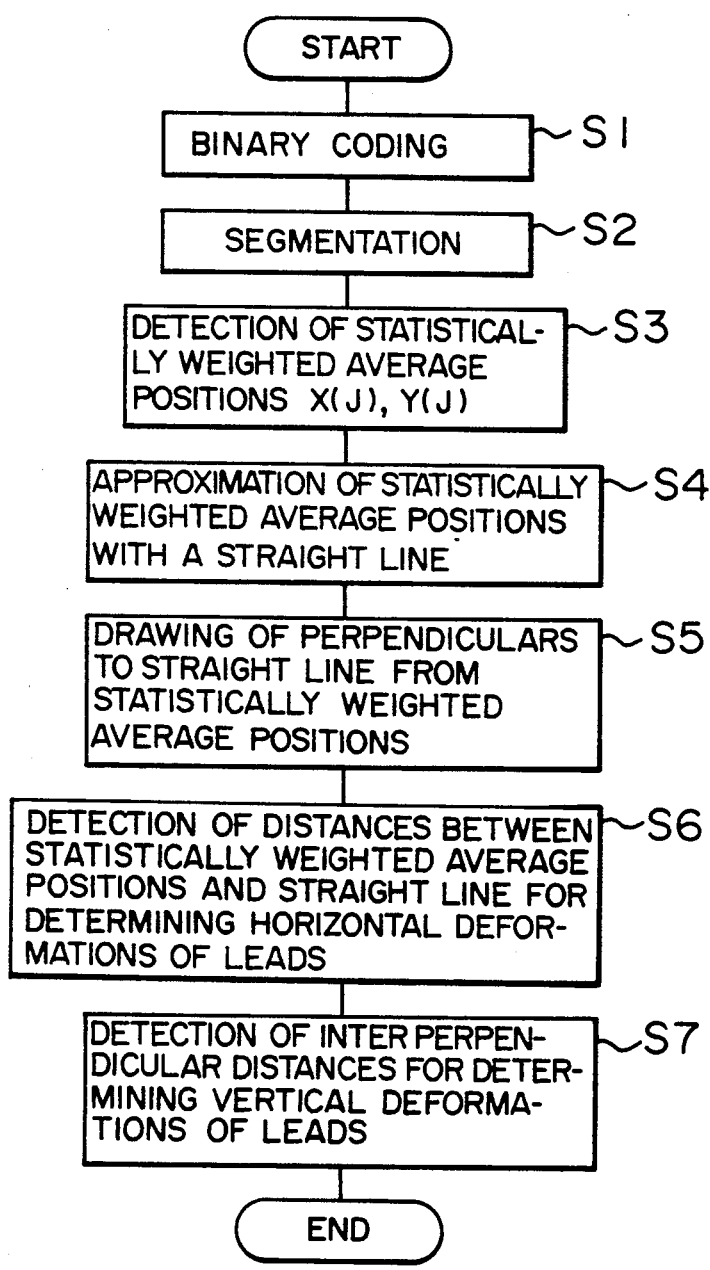
FIG. 11 is a flow chart showing a procedure for detecting the vertical and horizontal lead deformations.

FIG. 11 is a flow chart showing a procedure for detecting the vertical and horizontal lead deformations.

Referring to FIG. 11, at a step S1, the image data undergoes a binary coding processing. To this end, the data may be binary-coded with reference to a threshold level TH, as shown in FIG. 12A, by way of example.

At a step S2, the regions or sections of the individual leads illuminated with the sectioning light beam are determined on the basis of the binary-coded image data obtained at the step S1. Subsequently, segmentation is performed for determining a line 24 passing through the center of each illuminated lead region (refer to FIG. 12B).

At a step S3, for the line 24 extracted at the step S2, a statistically weighted average position X(J) in the X-direction (FIG. 10) is determined in accordance with the following expression:

$$X(J) = \frac{\sum_{I=L}^{N} M(I) \cdot I}{\sum_{I=L}^{N} M(I)}$$

where I represents a pixel value indicating a position of a pixel on the plane of the distributed image data outputted from the television camera, and M(I) represents brightness or intensity of the pixel at the position I, wherein only the brightness or intensities M(I) exceeding the level TH are used in the calculation of the statistically weighted average position X(J). Further, L and N are values for delimiting a range of the positions of the pixels involved in the above calculation. In this conjunction, it should be mentioned that a plurality of lines extending in parallel with the line 24 may be set, as exemplified by lines 24, 24' and 24" in FIG. 12B, whereon the above calculation may be performed on these lines. In that case, the statistically weighted average position can be determined with high accuracy while suppressing the influences of surface roughness of the lead and non-uniformity in the light reflecting state thereof to a minimum.

At a step S4, distribution of the statistically weighted average positions of the illuminated lead sections 22 are approximated by a straight line in accordance with a least square method (refer to a straight line 25 shown in FIG. 13).

At a step S5, perpendiculars are drawn to each of the statistically weighted average positions from the approximating line 25 (as indicated at Δl in FIG. 13).

At a step S6, distances Δl to each of the statistically weighted average positions X(J) from the approximating line 25 are determined (FIG. 13). By representing as θ the angular difference between the angle at which the leads are illuminated with the sectioning light beam and the angle at which the television camera 13 is oriented relative to the lower surface of the semiconductor device 11 (refer to FIGS. 5 and 6), the horizontal deformation of the lead can be determined on the basis of the quantities Δl and θ, as mentioned below.

In the case of the method shown in FIG. 5,
Δh = Δl/tan θ (refer to FIG. 7A).
In the case of the method shown in FIG. 6,
Δh = Δl/sin θ (refer to FIG. 8A).

At a step S7, distances K' between the adjacent perpendiculars K' drawn at the step S5 are determined (refer to FIG. 13). Then, the vertical deformation (misorientation) ΔK of the lead can be defined by the following expression:

$$\Delta K = |K' - K|$$

where K represents an inter-perpendicular distance for the normal or ideal leads suffering no vertical deformation.

Figure 14:
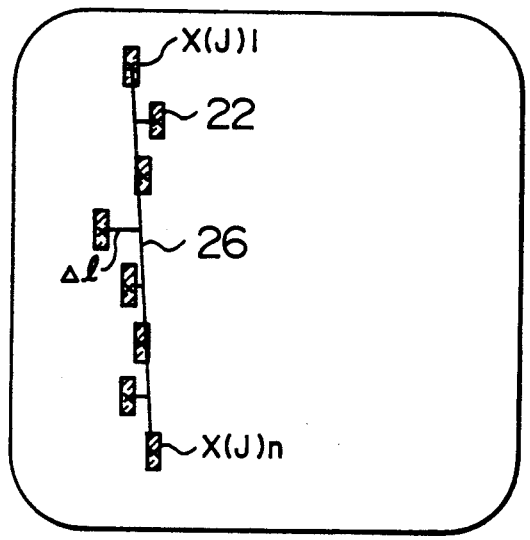
FIG. 14 is a view for illustrating another embodiment of the lead deformation detecting method according to the invention.

At this juncture, it should be mentioned that a method illustrated in FIG. 14 may be employed in place of the method of approximating the distribution of the statistically weighted average positions by the straight line 25 in accordance with the least square method. More specifically, referring to FIG. 14, both statistically weighted average position $X(J)_1$ and $X(J)_n$ located at the extremeties in the distribution of these positions X(J) are interconnected by a straight line 16, whereon perpendiculars are drawn to the straight line 26 from each of the other statistically weighted average positions. Subsequently, by determining the lengths Δl of the perpendiculars, it is possible to evaluate the leads as to whether they suffer from the vertical and/or the horizontal deformations. This method is advantageous in that the time taken for the calculation can be reduced because the least square method can be spared.

When the horizontal lead deformation Δh and the vertical lead deformation ΔK detected in this manner exceed respective reference values established previously, the semiconductor device having these leads is discarded as the inferior part. For practical application, the reference value for the horizontal lead deformation Δh may be set in a range of 0 to ±0.2 mm, while that for the vertical deformation ΔK may be set in a range of 0 to 0±50 μm. Obviously, these reference values may be established rather arbitrarily by the user of the device mounting apparatus, and the invention is never restricted to the reference values in the abovementioned ranges.

Figure 15:
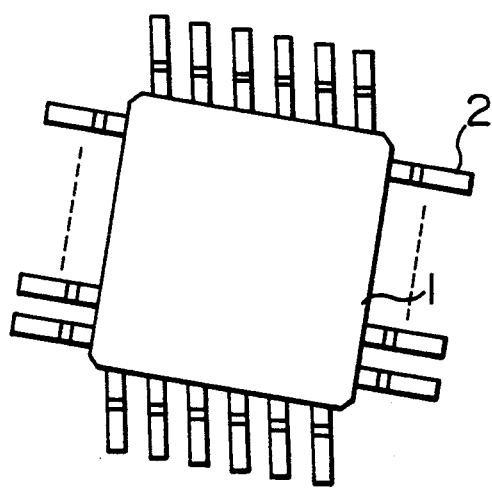
FIG. 15 is a view showing another example of the lead deformation in which all the leads attached to a semiconductor device along two sides thereof, respectively, suffer from vertical deformation or misorientation.

It may happen that all the leads projecting from one or more sides of a semiconductor device are vertically deformed or misoriented as a whole, as illustrated in FIG. 15. Even in such case, the deformation can be detected according to the teaching of the invention by virtue of the fact that the statistically weighted average positions of the leads at both ends of each side of the semiconductor device differ from the reference value in the relative sense.

In a modification of the embodiment shown in FIG. 5, the angle $\alpha$ at which the lead sectioning light beam is projected may be set smaller so that the angle $\theta$ becomes approximately equal to 90°. In this case, such image data can be obtained in which the quantity $\Delta l$ is magnified for a given magnitude of the horizontal lead deformation, whereby the latter can be detected with a higher accuracy. FIGS. 16A and 16B are views for illustrating a positional relation between the sectioning light beam 14 and the image pick-up device. As can be seen in these figures, the deviation $\Delta l$ of the illuminated section of a horizontally deformed lead from that of the normal lead can be given by $$\Delta l \approx \Delta h / \sin \alpha$$

where $\alpha$ represents the angle at which the leads are illuminated and $\Delta h$ represents the horizontal deformation. The above expression means that the deviation $\Delta l$ is magnified increasingly for a given value of $\Delta h$ as the angle $\alpha$ becomes smaller.

When the angle $\theta$ is 90°, the deviation $\Delta l$ can be picked up with a maximum magnification. This can be realized in such arrangement in which the images of the illuminated lead sections are picked up from the position substantially right below the semiconductor device with the small value of the light beam projection angle $\alpha$. The arrangement where the angle $\theta$ is selected substantially equal to 90° with the sectioning beam projection angle being reduced is well suited for detection of a minute horizontal deformation because of the magnifying feature described above.

As will now be appreciated from the foregoing, reliability of the lead connection upon mounting a semiconductor device on a printed wiring substrate can significantly be increased by detecting the vertical and/or horizontal deformation of the leads of the semiconductor device before mounting thereof on the printed substrate according to the teachings of the present invention. Besides, by using the lead sectioning light beam, the vertical and/or horizontal deformation of the lead of a semiconductor device can be detected within a short time. Furthermore, by applying the teaching of the invention to the semiconductor device mounting apparatus, one and the same detector can be operated both as a detector for detecting the position of the semiconductor device and a detector for detecting the positions of the illuminated lead sections. Thus, there can be realized inexpensively an apparatus for detecting horizontal and/or vertical deformation of the leads of a semiconductor device with a remarkably high accuracy.

What is claimed is:

1. A method of detecting horizontal and/or vertical deformation of leads of a semiconductor device, comprising steps of:
    illuminating leads of a semiconductor device with a planar light beam;
    picking up images of regions of said leads illuminated with said planar light beam by means of image pick-up means;
    arithmetically determining statistically weighted average positions of the illuminated lead regions picked up by said image pick-up means; and
    detecting at least one of vertical deformation and horizontal deformation of said leads on the basis of distribution of said statistically weighted average positions.

2. A method of detecting lead deformations in a semiconductor device, comprising:
    a step of illuminating leads of a semiconductor device with a planar light beam;
    a step of picking up images of the leads illuminated with said planar light beam by means of image pick-up means and binary-coding image data of the regions of said leads illuminated with said planar light beam and outputted from said image pick-up means;
    a step of determining the regions of the individual leads illuminated with said planar light beam on the basis of the binary coded image data and determining lines each passing through a center position of each of said regions illuminated with said planar light beam;
    a step of determining statistically weighted average positions in respect to brightness of said regions illuminated with said planar light beams relative to said line;
    a step of approximating the distribution of the statistically weighted average positions of said illuminated regions by a straight line;
    a step of drawing perpendiculars to said statistically weighted average positions, respectively, from said approximate straight line; and
    a step of determining distances to said statistically weighted average positions, respectively, from said approximate straight line.

3. A method of detecting lead deformations in a semiconductor device, comprising:
    a step of illuminating leads of a semiconductor device with a planar light beam;
    a step of picking up images of the leads illuminated with said planar light beam by means of image pick-up means and binary-coding image data of the regions of said leads illuminated with said planar light beam and outputted from said image pick-up means;
    a step of determining regions of the individual leads illuminated with said planar light beam on the basis of the binary coded image data and determining lines each passing through a center position of each of said regions illuminated with said planar light beam;
    a step of determining statistically weighted average positions in respect to brightness of said regions illuminated with said planar light beams relative to said line;
    a step of approximating the distribution of the statistically weighted average positions of said illuminated regions by a straight line;
    a step of drawing perpendiculars to said statistically weighted average positions, respectively, from said approximate straight line; and
    a step of determining distances between adjacent ones of said perpendiculars, respectively, to thereby determine magnitude of the vertical deformation of the leads of said semiconductor device.

4. A method of detecting lead deformations in a semiconductor device, comprising:
    a step of illuminating leads of a semiconductor device with a planar light beam;
    a step of picking up images of the leads illuminated with said planar light beam by means of image pick-up means and binary-coding image data of the regions of said leads illuminated with said planar light beam and outputted from said image pick-up means;

a step of determining regions of the individual leads illuminated with said planar light beam on the basis of the binary coded image data and determining lines each passing through a center position of each of said regions illuminated with said planar light beam;

a step of determining statistically weighted average positions in respect to brightness of said regions illuminated with said planar light beams relative to said line;

a step of approximating the distribution of the statistically weighted average positions of said illuminated regions by a straight line;

a step of drawing perpendiculars to said statistically weighted average positions, respectively, from said approximate straight line;

a step of determining distances to said statistically weighted average positions, respectively, from said approximate straight line; and a step of determining distances between adjacent ones of said perpendiculars, respectively, to thereby determine magnitude of the vertical deformation of the leads of said semiconductor device.

5. An apparatus for detecting deformation of leads of a semiconductor device, comprising:

planar light beam generating means for illuminating the leads of the semiconductor device with a planar light beam;

image pick-up means for picking up images of said leads and for outputting image signals;

image processing means for receiving and processing said image signals; and said image processing means being imparted with a function for arithmetically determining statistically weighted average positions of the planar light beam on said individual leads on the basis of said image signals, to thereby detect at least one of vertical and horizontal deformation of said leads on the basis of said statistically weighted average positions.

6. A method of detecting horizontal and/or vertical deformation of leads of a semiconductor device, comprising the steps of:

illuminating leads of the semiconductor device with a planar light beam having an optical axis;

picking up images of regions of said leads illuminated with said planar light beam by means of image pick-up means; and detecting at least one of the vertical deformation and the horizontal deformation of said leads on the basis of distributed data of said illuminated regions of the individual leads picked up by said image pick-up means;

wherein, in said illuminating, an angle of an optical axis along which said planar light beam is projected onto soldering surfaces of said leads is selected to be smaller than 90°, and wherein, in said detecting, an angle between said optical axis of said planar light beam and that of said image pick-up means is selected to be approximately 90°.

7. A semiconductor lead deformation detecting method according to claim 6, wherein said distributed data of said illuminated regions of the individual leads are determined on the basis of differences between image data of said leads picked up before illuminating said leads with said planar light beam and image data of said leads picked up under illumination with said planar light beam.

8. An apparatus for detecting deformation of leads of a semiconductor device, comprising:

planar light beam generating means for illuminating the leads of the semiconductor device with a planar light beam having an optical axis;

image pick-up means for picking up images of said leads and for outputting image signals; and image processing means for receiving and processing said image signals;

wherein the optical axis of said illuminating means is projected onto soldering surfaces of said leads at an angle smaller than 90°, and wherein an angle between said optical axis of said planar light beam and that of said image pick-up means is approximately 90°.

9. An apparatus for detecting deformations of leads of a semiconductor device according to claim 8, wherein said planar light beam generated by said planar light beam generating means is monochromatic, and wherein said image pick-up means picks up images of the leads of the semiconductor device through a filter which passes therethrough only those light rays which result from reflection of said monochromatic planar light beam on said leads.

* * * * *